United States Patent [19]

Milosevic et al.

[11] Patent Number: 5,262,845
[45] Date of Patent: Nov. 16, 1993

[54] OPTICAL ACCESSORY FOR VARIABLE ANGLE REFLECTION SPECTROSCOPY

[75] Inventors: Milan Milosevic, Fishkill; Nicolas J. Harrick, Ossining, both of N.Y.

[73] Assignee: Harrick Scientific Corporation, Ossining, N.Y.

[21] Appl. No.: 894,991

[22] Filed: Jun. 8, 1992

[51] Int. Cl.⁵ ............................................. G01N 21/01
[52] U.S. Cl. ..................................... 356/445; 356/244
[58] Field of Search ............... 356/300, 346, 244, 445, 356/446

[56] References Cited

U.S. PATENT DOCUMENTS

| | | | |
|---|---|---|---|
| 4,657,390 | 4/1987 | Doyle | 356/346 |
| 5,048,970 | 9/1991 | Milosevic et al. | 356/244 |
| 5,106,196 | 4/1992 | Brierley | 356/445 |
| 5,177,561 | 1/1993 | Milosevic et al. | 356/244 |

Primary Examiner—F. L. Evans

[57] ABSTRACT

A variable angle reflection accessory for use in reflection spectrometry characterized by a pair of fixed ellipsoidal reflectors positioned inside an enclosure adjacent a sample surface on the outside of the enclosure and a pair of rotatable plane mirrors positioned at opposite sides of the sample surface. The spectrometer beam is brought to a focus at the first plane mirror, from which it is reflected off the first ellipsoidal reflector to a focus at the sample surface. The reflected beam follows a corresponding path back to the spectrometer. Rotating the mirrors in unison causes the beam angle of incidence on the sample surface to vary over a wide range while maintaining optical alignments and continuing to center the radiation on the same sample area. The outside positioning of the sample surface allows the accessory to be easily coupled to a purge port of the spectrometer and allows rapid sample exchanges without breaking the purge atmosphere.

17 Claims, 7 Drawing Sheets

OPTICAL ACCESSORY FOR VARIABLE ANGLE REFLECTION SPECTROSCOPY

This invention relates to variable angle reflection spectroscopy, and in particular to an accessory for use therein.

BACKGROUND OF THE INVENTION

Variable angle reflectance is an important spectroscopic technique. Certain samples, such as opaque substances, films on opaque substrates, and films on liquids, are tedious or practically impossible to analyze with conventional transmission spectroscopy equipment. The analyses of such samples by reflection spectroscopy, however, are straightforward.

There are three different methods of reflection spectroscopy. The technique employed depends on the sample nature and the information sought. External reflection spectroscopy is used with thin films on opaque substrates and opaque smooth solids. Internal reflectance permits spectral measurements of liquids, powders, pastes, gels, and soft solids. Diffuse reflectance is most commonly used for the analysis of powders and rough surface solids. Variable angle studies, using either external or internal reflection spectroscopy, provide data for the determination of optical constants and sample thicknesses. For further background on the state of the art of this technology, reference is had to U.S. Pat. No. 3,603,690, and the Harrick Scientific Corporation catalog HSC-831 which describes a number of the currently available reflection accessories.

In our earlier-issued patent, U.S. Pat. No. 5,048,970 ('970), the contents of which are hereby incorporated by reference, we describe and claim a variable angle reflection accessory for use in reflectance spectroscopy which offers a number of important benefits in the field, such as the ability to vary the angle of incidence on the sample over a very wide range while maintaining optical alignment and continuing to center the radiation beam on the same sample area, and a rotation mechanism providing a linear relationship between user rotation of a knob and the resultant change in the angle of incidence. In this accessory, the sample holder is provided inside the accessory interior.

In our copending application, Ser. No. 07/831,529, now U.S. Pat. No. 5,177,561, the contents of which are hereby incorporated by reference, we describe a novel accessory construction for use in the sampling compartment of conventional spectrometers that allows the accessory to be coupled directly to the purge system of the spectrometer, so that the entire optical path lies in an absorption-free atmosphere. With certain accessories, where the sample is also mounted external to or on the outside of the accessory housing, this can offer the further advantage that samples are easily exchanged without breaking the purge seal thereby greatly increasing sample analysis throughput. This is important for certain users. This benefit, however, cannot be obtained with the variable angle reflectance accessory described in the '970 patent because of the location of the sample holder inside the accessory housing.

SUMMARY OF THE INVENTION

An object of the invention is a variable angle reflection accessory in which the sample can be mounted on the outside of the accessory housing.

A further object is a variable angle reflectance accessory that can be used with the purge system described in the copending application to obtain the benefits thereof.

Another object of the invention is a variable angle reflection accessory that is easily adapted for all three reflection techniques and that can be operated over a broad range of incident angles, while maintaining optical alignment and continuing to center the incident radiation on the same sample area.

These and other objects and advantages as will appear hereinafter are achieved by an accessory which provides for holding the sample to be analyzed on an external surface and which is configured to be placed in the sampling compartment of a conventional spectrometer. In accordance with one aspect of the invention, the sample-receiving surface on a variable angle reflectance accessory is provided on an external surface of the accessory housing. The incident radiation beam from the spectrometer is directed to one of two back-to-back plane mirrors mounted approximately in the enclosure center and which are rotatable in unison. After reflection from the one mirror, the radiation beam is directed to an ellipsoidal segment reflector which re-directs and focusses the beam toward a window in the enclosure wall. The sample is mounted over the window. The return beam follows a symmetrical path and is restored with its original focus condition to the path from the spectrometer output port to its input port leading to the spectrometer detector and signal processing circuitry. As in the '970 patent, the two rotatable mirrors are coupled together and rotate equal amounts but in opposite directions. By rotating the coupled plane mirrors, the angle of incidence of the beam on the sample can be varied over a very wide angle. In addition, the beam can be maintained by the optics centered on the sample while maintaining the focusing and alignment conditions of the spectrometer.

In accordance with another aspect of the invention, a novel mechanism is provided to rotate the two mirrors in unison. This mechanism provides a linear relationship between a rotatable knob operable by the user and rotation of the mirrors. In a preferred embodiment, the mechanism employs an internal arcuate slot cooperating with an engaging pin to provide the desired linear relationship.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

DETAILED DESCRIPTION OF THE PREFERRED EMBODIMENTS

Any of many conventional spectrometers can be employed with the variable angle reflection accessory of the invention. The conventional spectrometer contains a sampling compartment for receiving the sample to be analyzed together with suitable optics components for directing the radiation beam emanating from a port of the spectrometer to the accessory and re-directing the beam after interaction with the sample back into the spectrometer for detection and processing of the resultant electronics signals.

The typical spectrometer beam converges to a small area or point more or less at the center of the sampling compartment and from that point diverges until it reenters the spectrometer. Ideally, one wants to maintain this focussing condition even though an accessory may be present which extends the optical beam path.

Figure 1:
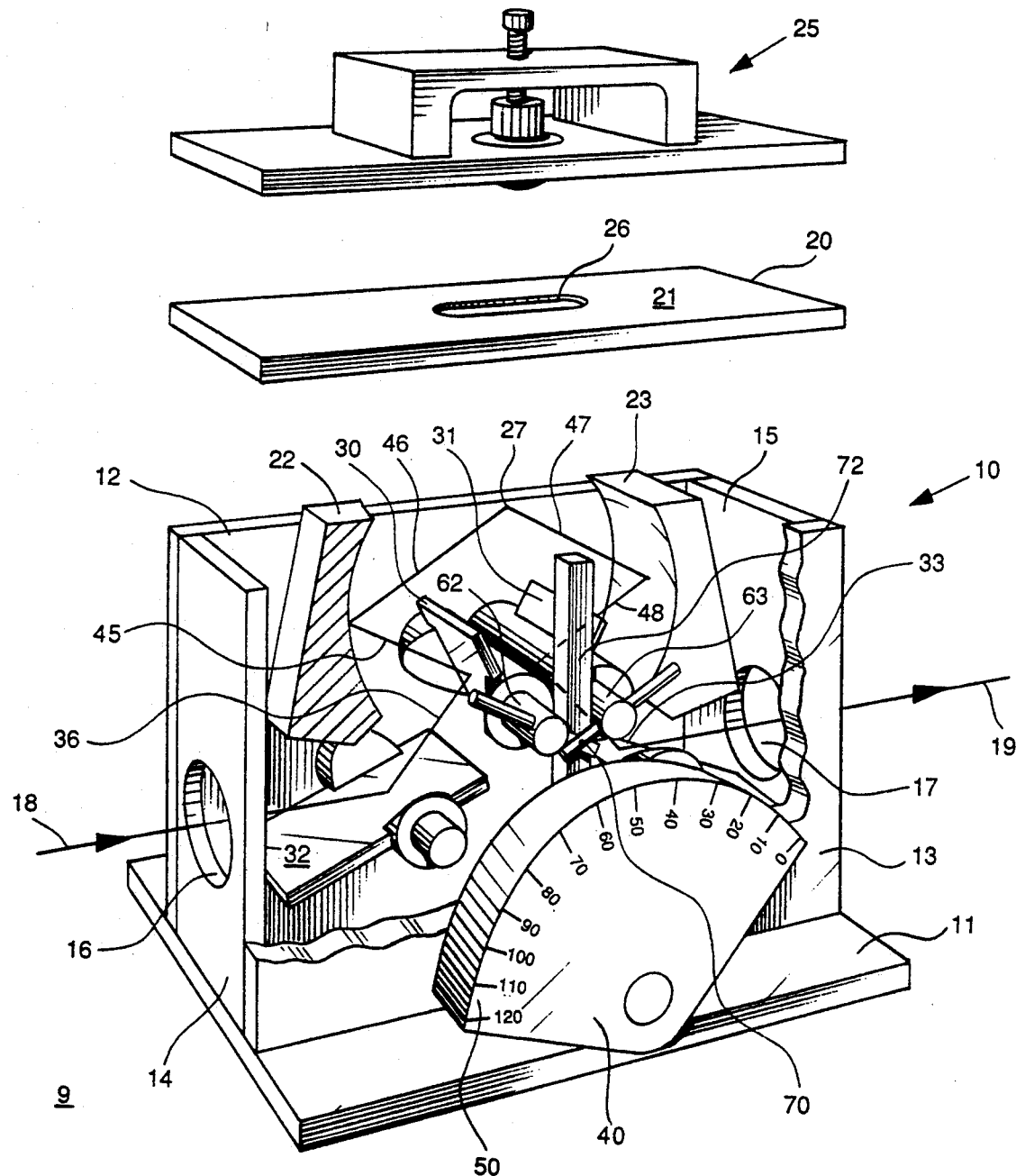
FIG. 1 is a perspective, partially exploded view of one form of variable angle reflection accessory in accordance with the invention, shown with an enclosure side broken away to show the interior.

FIG. 1 illustrates one form of accessory of the invention which not only maintains the focussing conditions but in addition maintains the beam alignment, with the result that the optical paths within the spectrometer require no changes. The accessory comprises an enclosure 10 which houses the optical components and provides the sample support. The enclosure 10 comprises a base member 11 which simply rests on the surface of the sampling compartment 9, a rear vertical wall member 12 which supports the optical components, a front wall 13 which supports a knob 40 for changing the angle of incidence, side walls 14, 15 with ports 16, 17 for an entering radiation beam 18 and an exiting radiation beam 19, and a top wall 20 whose outer surface acts as a sample support surface 21. Over the top wall 20 may be provided a pressure-applying mechanism 25 for pressing the sample lying underneath against the sampling surface 21. To allow a radiation beam from the accessory interior to access the sample, a window 26 is provided at the center of the top wall 20. The sample would typically be placed over the window 26 and close off the window. First and second ellipsoidal mirror segments 22, 23 are mounted on the wall 12. The ellipsoidal mirrors 22, 23 are located under the window 26 to the left and to the right of the latter, and are positioned to have a common focal point 27 at the center of the surface of a sample placed over the window 26. Two rotatable mirrors 30, 31 are mounted also on the wall 12 at opposite sides of the window 26. The mechanism for rotating them in unison is located adjacent the front wall 13, and is not visible in FIG. 1. Two fixed plane mirrors 32, 33 are mounted on the rear wall 12, again at opposite sides of the window 26.

The typical converging beam 18 from the spectrometer is incident on the plane mirror 32, from which it is reflected 36, still converging, to the first movable mirror 30. Had the accessory not been present, the undeflected beam would focus to a point at the center, and then diverge and continue back into the spectrometer. The positions of the plane mirrors 32, 30 are chosen such that the optical path remains the same so that reflected beam 36 also focusses to a point (not shown) at approximately the center of the first movable mirror 30. That latter point is also a focus of the ellipsoidal mirror 22. Therefore, the beam 45 reflected from the first movable mirror 30 onto the surface of the first ellipsoidal mirror 22 will upon reflection 46 be reimaged from the latter at the focal point 27 at the window 26.

The optical path of the beam after interaction with a sample is similar. Thus, the beam 47 from the sample upon reflection 48 from the second ellipsoidal mirror 23 is re-focussed at a point approximately at the center of the second movable mirror 31. From there, the reflected beam 51 reflects off of the mirror 33, and is now back in the same optical path 19 to the spectrometer that the beam would have had in the absence of the accessory. The post-sample optical path has the same optical length as the pre-sample optical path.

The function of the first ellipsoidal mirror 22 is to refocus the beam from the first movable mirror 30 to the sampling window 26, and the second ellipsoidal mirror 23 collects the radiation reflected from the sample and refocuses it at the second movable mirror 31.

It will be evident from the foregoing description that it is desirable from the user's standpoint that a certain rotation or revolution of the knob 40 will produce the same change in the angle of incidence over the full range of variable angles possible with this accessory, i.e., about 30°–85°, using a linear scale 50. The advantage would be that the user could then easily interpolate angle positions from the angle positions displayed on the scale, and a vernier indicator could easily be added for even finer adjustments. Similarly to the accessory described in the '970 patent, the accessory of the present invention has the ability to continuously vary the incident angle on the sample over a wide range from about 30° to 85° without misaligning the system. This is an important feature of the invention, because spectra measured at different angles can be obtained under the same conditions and can be quantitatively compared. Furthermore, since changing the angle of incidence does not require repositioning the sample, the sample can easily be enclosed in a chamber with controlled conditions, such as temperature, pressure, and/or atmosphere.

In addition, in accordance with the invention, with changes in the incident angle, the focal point of the incident beam remains always on the sample and reflects from the same area of the sample. This minimizes the required sample area and also permits examination of samples with a moderate curvature. Furthermore, areas of special interest, such as contaminants or surface defects, may be isolated for analysis. A further feature is that, since changing the angle of incidence does not require repositioning of the sample, liquid samples which require horizontal positioning are easily handled.

A further feature of the invention is that the polarization of the incident light does not vary with changes in the incident angle. This is important, since reflectance depends on the polarization of the incident light. In order to compare the experimental measurements to theoretical expressions, the polarization of the incident light must be know. This is easily achieved with the accessory of the invention.

Another important feature of the invention is its versatility and flexibility. The accessory can be used for a number of different reflectance spectroscopy techniques, including external, internal, bidirectional external, and in-line diffuse reflection.

Further, since the sampling surface can be positioned horizontally and is unobstructed and thus easily accessible, many different kinds of samples can be analyzed, such as large panels.

Finally, the external sampling position allows the accessory's use with the purge system described in the copending application, which permits rapid sample exchange and changes in the incident angle with minimal or no disruption of the purge of the system.

Figure 5:
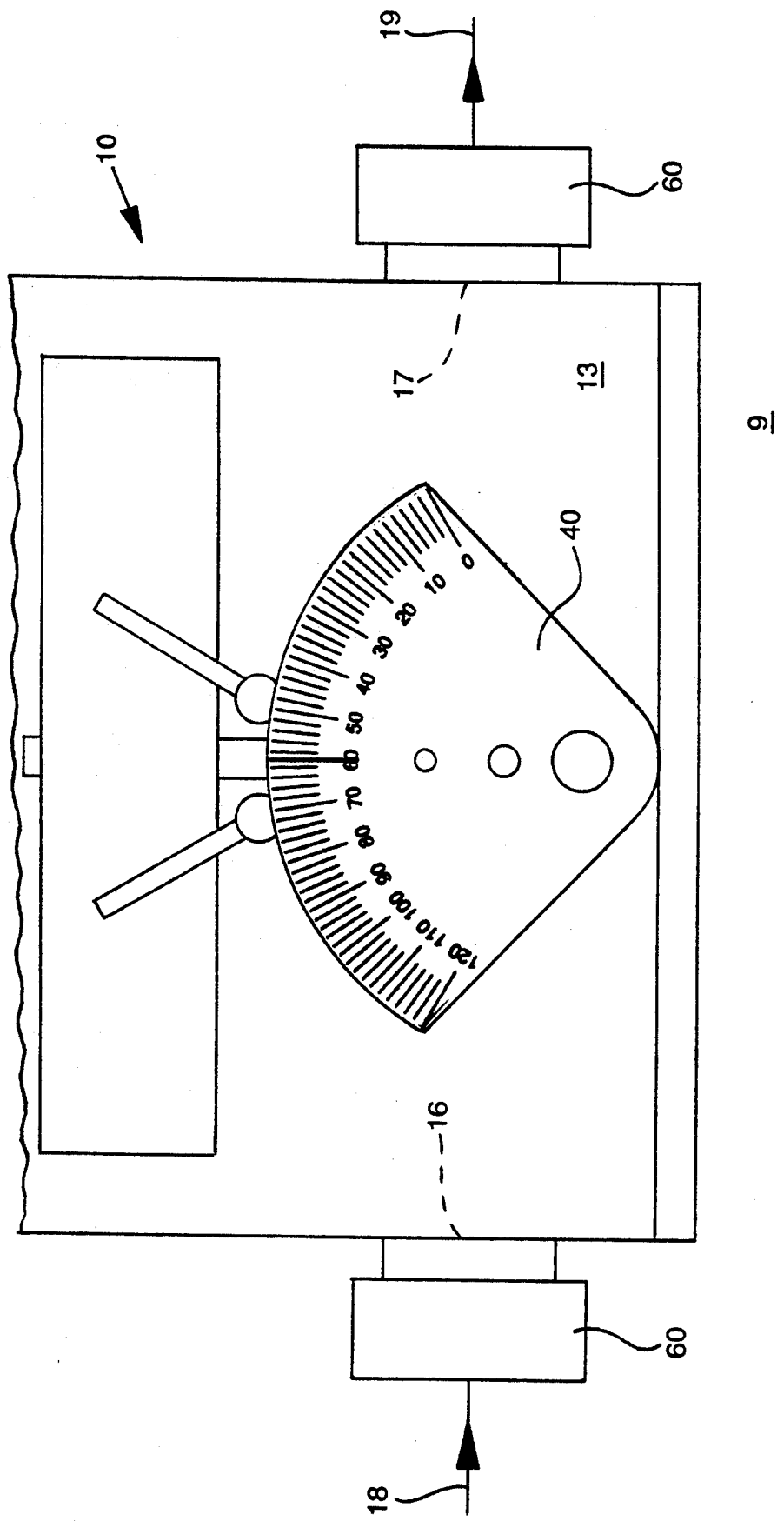
FIG. 5 is a view similar to FIG. 2A showing the accessory of FIG. 1 adapted to be coupled to the spectrometer purge system.

FIG. 5 depicts one suitable arrangement. Adaptors 60 can be provided at the entrance 16 and exit 17 ports, and hose or tube couplings (not shown) provided for connecting to the spectrometer beam/purge ports. Alternatively, a purge source can be coupled to a standard fitting (not shown) provided at the housing side. Any leakage where the sample closes off the window is no problem since the purge pressure typically exceeds atmospheric pressure so the leak, if any, is of the purge gas out. Reference is had to the referenced application for more details on the coupling.

Figure 2A:
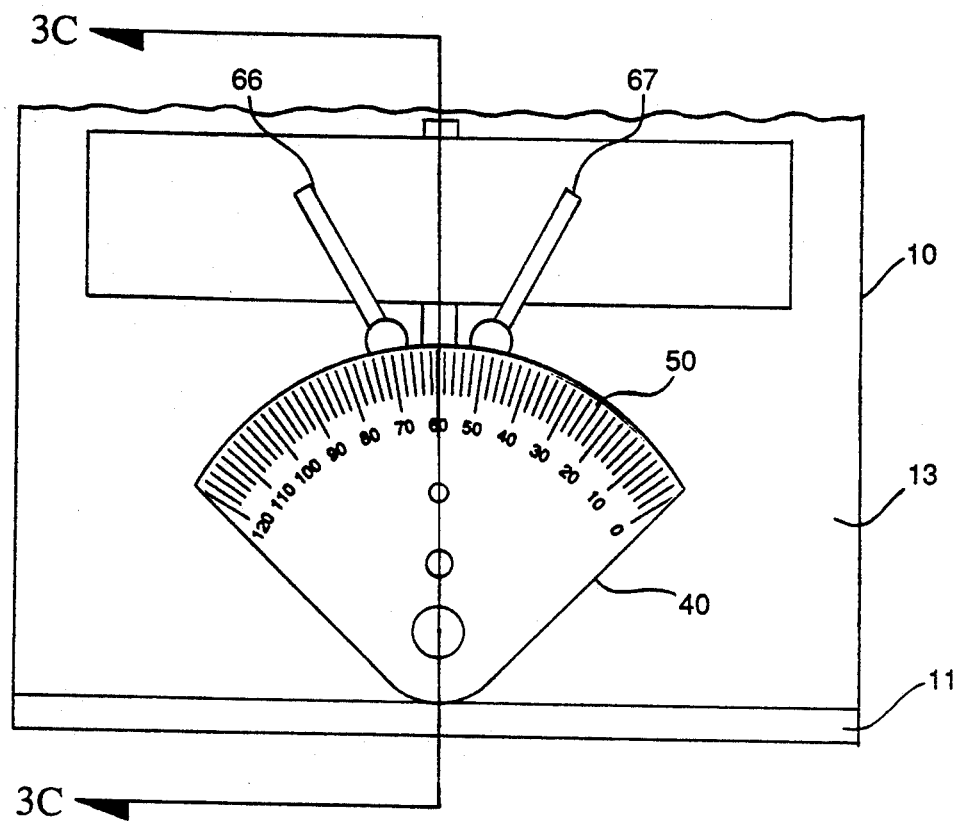
FIGS. 2A and 2B front and side views of the accessory of FIG. 1 in assembled condition but with the top omitted.
Figure 2B:
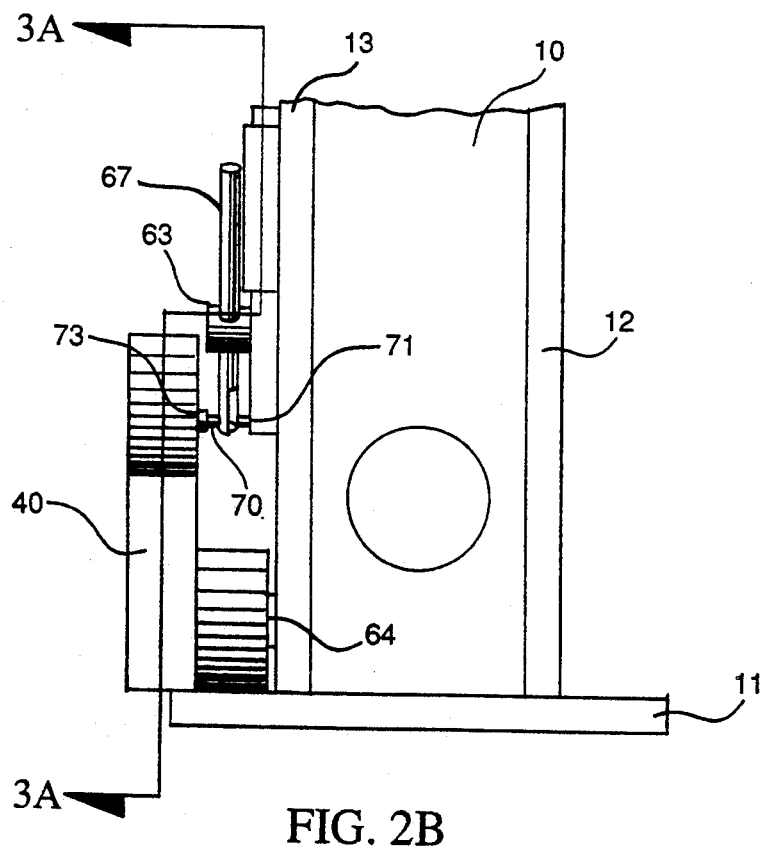
Figure 3A:
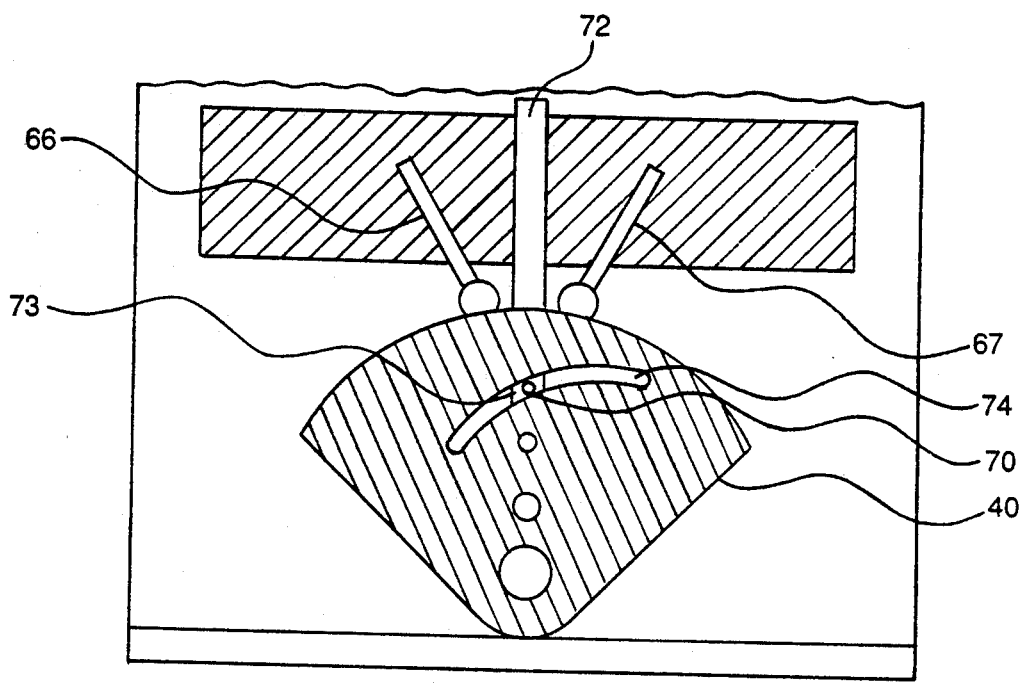
FIGS. 3A and 3B are cross-sectional views taken along the line 3A—3A of FIG. 2B to illustrate a suitable mechanism for rotating the plane mirrors in unison in two different positions.
Figure 3B:
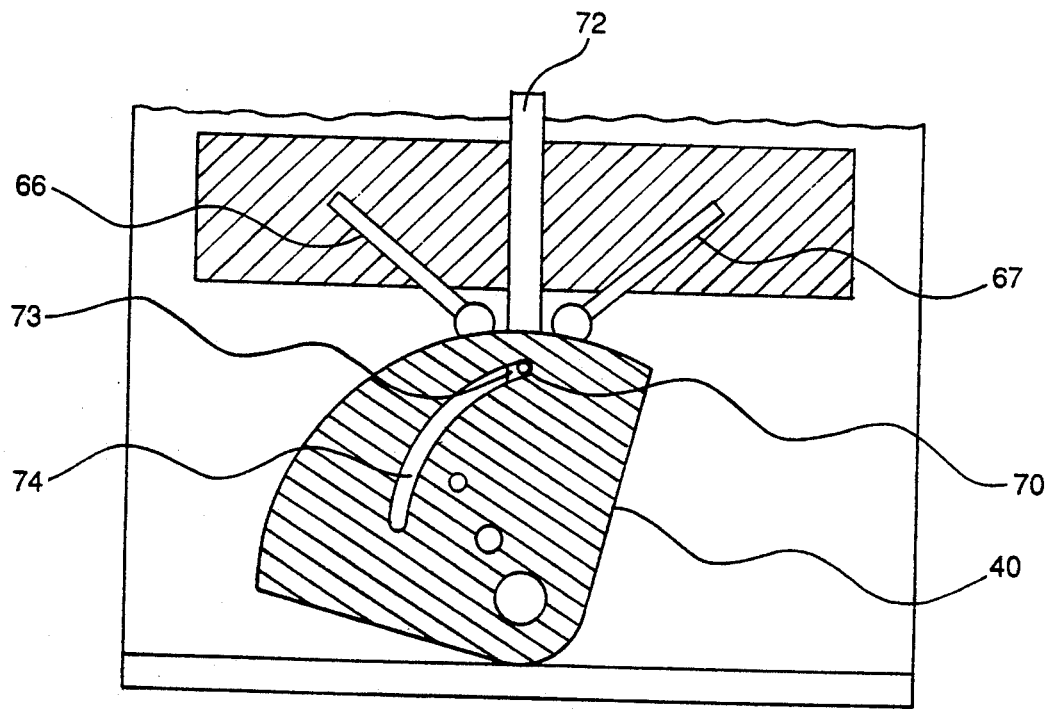
Figure 3C:
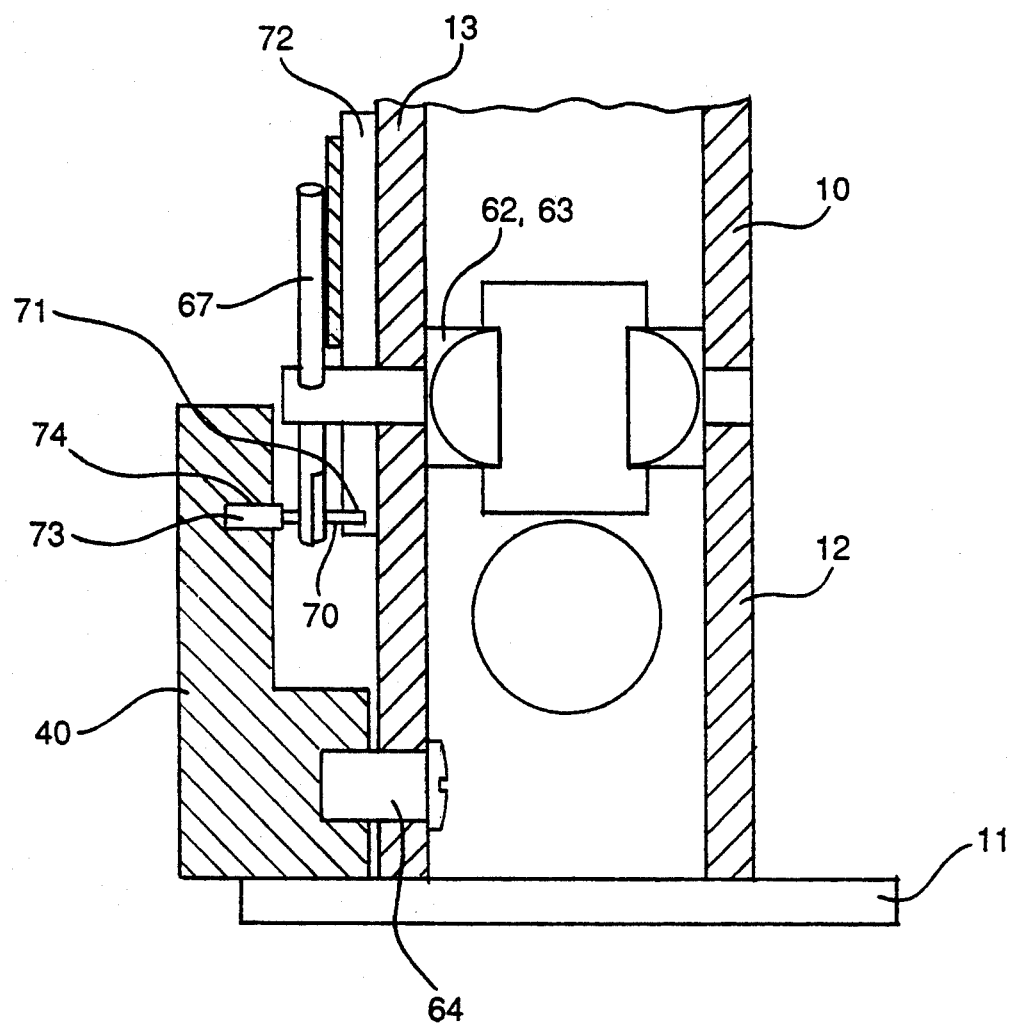
FIG. 3C is a cross-sectional view taken along the line 3C—3C of FIG. 2A.

FIGS. 2A and 2B are, respectively, a view of the front and of the side of the accessory enclosure (the top is not shown) showing the mechanism which couples the mirrors 30, 31 to rotate together, in mirror image fashion. The mechanism comprises rotatable shafts 62, 63 for the two mirrors 30, 31 mounted for rotation on the back wall 12. The knob 40, in turn, is mounted on a pin 64 for rotation in the front wall 13. First and second pins 66, 67 engage and are fixed to each of the shafts 62, 63. The pins 66, 67 are transverse to their respective shaft and are positioned at about 45° to the left and right, respectively, of a vertical plane. As shown more clearly in FIGS. 1 and 3C, the lower adjacent pin ends cross and are pinned together by a third pin 70 is extending parallel to the shafts 62, 63. The inward end of the pin 70 is anchored at 71 in a post 72 on the front wall 13. The outward end of the third pin 70 is enlarged to form a block 73 with top and bottom surfaces that match and fit within and engage the sides of an arcuate slot 74 machined on the inside of the knob 40. When the knob 40 is rotated, the slot 74 walls cams the block 73 causing it to rotate also. It, in turn, drives the crossed first and second pins 66, 67 to which it is fixed. FIG. 3A shows the position of the parts in the neutral position, with the knob centered, producing a 60° angle of incidence of the beam on a specimen over the window 26. Rotation of the knob 30° CCW, shown in FIG. 3B, rotates the left mirror 30 CCW and the right mirror 31 CW an equal amount, so the angle of incidence is now reduced to 30°. Similar but reverse operation occurs when the knob is rotated CW.

The mechanism is basically a simple mechanical angle divider, with the parameters of the divider chosen to provide direct correspondence between the angle of incidence on the sample and the rotation of the angle select knob 40. These parameters include the curvature of the slot 74 and the first and second pin dimensions. A suitable choice is readily made by anyone skilled in the art to provide the desired direct correspondence and thus a linear relationship between the knob angular rotation and angle of incidence change. This allows a linear scale 50 to be provided on the knob, which enables the precision of the angle readout to be increased via, for example, vernier devices, and simplifies motorizing the angle exchange if desired.

It will be evident that, while the mechanism described is preferred, the invention is not limited thereto, and other suitable driving mechanisms can be substituted.

Summarizing, it is desirable from the user's standpoint that a certain rotation or revolution of the knob 40 will produce the same change in the angle of incidence over the full range of variable angles, i.e., 30°-85°, using a linear scale 50. The advantage would be that the user could then easily interpolate angle positions from the angle positions displayed on the scale, and a vernier indicator could easily be added to the pointer for even finer adjustments.

When the knob 40 is thus rotated, it causes the beam 45 to scan over the length of the ellipsoidal segment 22, as in the '970 patent. The result is to cause the reflected beam 46 angle of incidence on the sample 20 to vary. The property of the ellipse which maintains the focusing conditions between the focal point on the mirror 30 and the focal point 27 at the sample preserves the optical alignment and focussing conditions for any selected incident angle so long as the beam 45 is incident on the ellipsoidal surface 22. The corresponding beam paths and optical alignment also takes place between the sample, the second ellipsoidal mirror 23 and the second movable mirror 31. As is evident, with respect to a vertical plane perpendicular to the wall 12 and passing through the sample focus 27, the optical system to the right of the sample support 20 is a mirror image of that to the left.

Figure 4A:
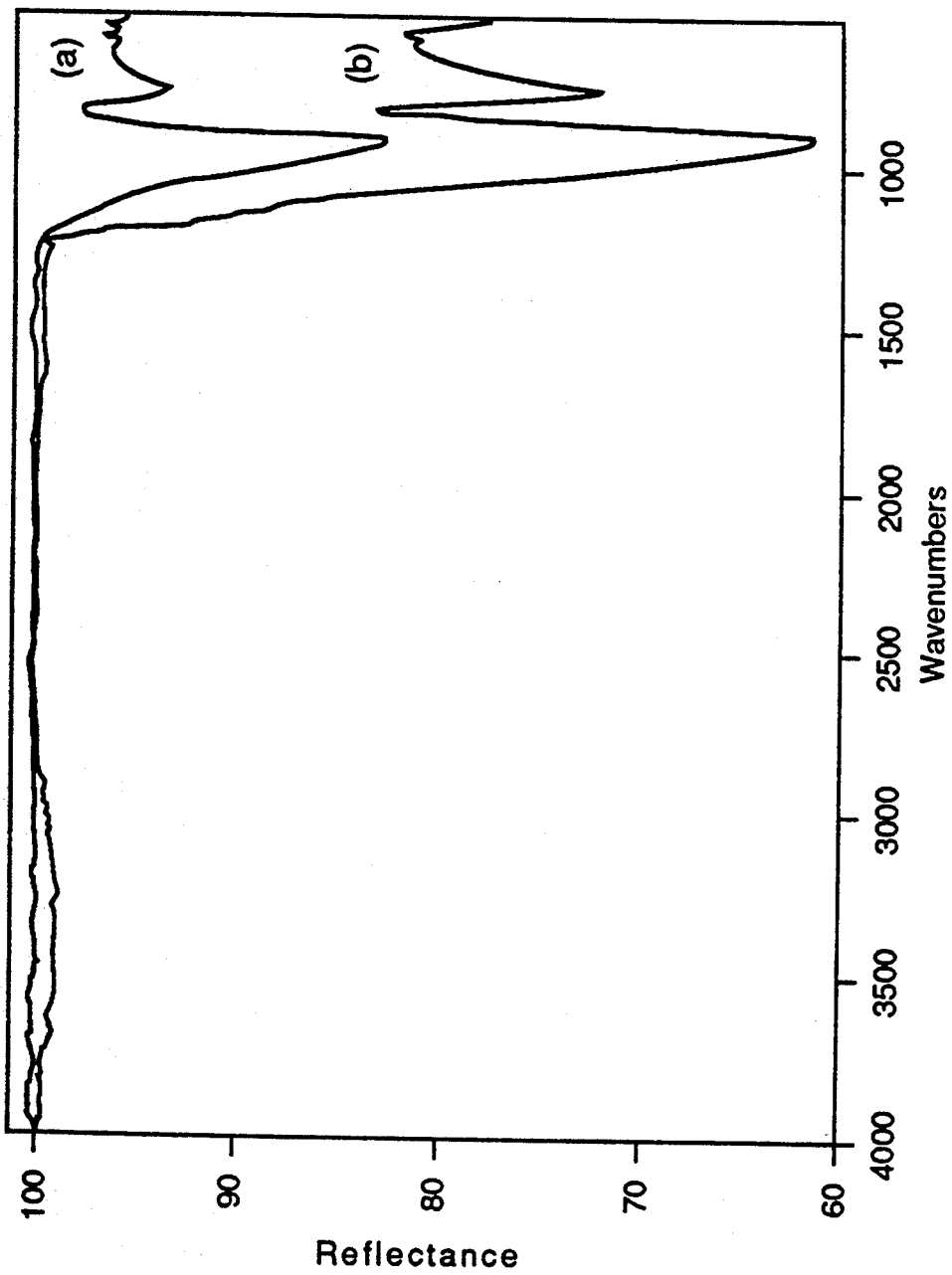
FIGS. 4A and 4B show sample spectra obtained with the accessory of the invention.
Figure 4B:
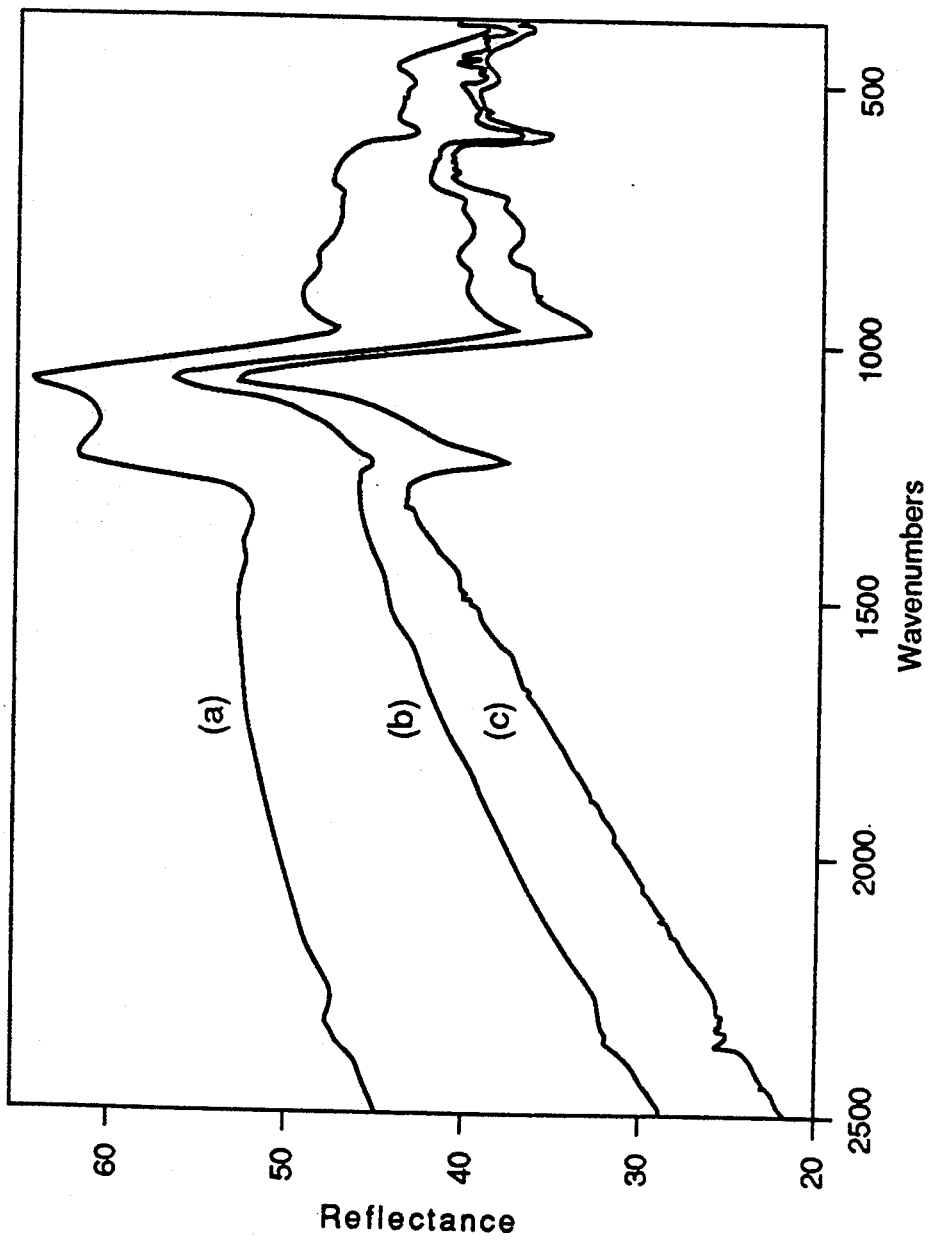

Some applications taken with the accessory of the invention are illustrated in FIGS. 4A and 4B. The results presented were obtained with a Mattsom Sirius 100 FT-IR spectrometer. For the internal reflection studies, the internal reflection element was of ZnSe. FIG. 4A shows spectra of glass taken at incident angles of (a) 80° and (b) 50°. FIG. 4B shows spectra of coated Si recorded at incident angles of (a) 80°, (b) 60°, and (c) 40°.

The advantage of being able to operate over a broad range of incident angles is illustrated by these sample spectra. Note that the spectral sensitivity depends strongly on incident angle, as expected.

It is also possible to record variable angle reflection spectra from samples which are difficult to examine due to sample form or size. Liquid samples, for example, fall into this category since such samples are typically mounted vertically. In the accessory of the invention, however, the sampling surface is horizontal and exposed. This simplifies sample mounting. In addition to liquids, small samples pose problems in variable angle reflectance. Traditional variable angle reflection accessories do not probe the same area of the sample when the incident angle is varied. With small samples, recording spectra at various incident angles can require repositioning the sample for different incident angles. The accessory of the invention, however, always centers the incident radiation on the same sample area, eliminating the need to move the sample.

In addition to the uses of the accessory of the invention for external and internal reflectance, the accessory of the invention can also be adapted to carry out diffuse reflection measurements.

In summary, a new variable angle reflection accessory has been described, which is versatile and which is easily reconfigured for the three different reflection techniques. It is useable over a large range of incident angles without requiring realignment or repositioning of the sample. Thus, this new accessory is a flexible and versatile addition to the field of reflection spectroscopy.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A variable angle reflection accessory for use in reflection spectrometry, comprising:

an enclosure having an outside wall, said outside wall including radiation-transmissive means for supporting on said outside wall a sample having a surface to receive a radiation beam, first and second ellipsoidal segment reflectors mounted inside the enclosure adjacent the said outside wall and in positions at first and second sides, respectively, of the sample supporting means such that each ellipsoidal segment defines a first focus substantially at the location of a sample surface and a second focus at, respectively, the first and second sides, first and second plane reflectors mounted inside the enclosure and positioned, respectively, at the first and second sides with its reflecting surface at the location, respectively, of the second focus, optical means for directing a converging beam of radiation to the first plane reflector and for directing a diverging radiation beam from the second plane reflector, means for rotating the first and second plane reflectors in unison thereby to change the angle of incidence of the radiation beam on a sample surface.

2. A variable angle reflection accessory as claimed in claim 1, wherein the optical means for directing the converging beam of radiation comprises a plane reflector.

3. An accessory as claimed in claim 2, wherein the said optical means brings the converging radiation beam to a focus on the first plane reflector at the position of the said second focus of the first ellipsoidal reflector.

4. A variable angle reflection accessory as claimed in claim 3, wherein the optical means for directing the diverging beam is identical to and a mirror image of the optical means for directing the converging beam.

5. The accessory of claim 1, wherein the enclosure outside wall has at the sample supporting means a window serving as the radiation-transmissive means for allowing the radiation beam to access the sample.

6. The accessory of claim 1, wherein the enclosure outside wall is a top horizontally oriented wall having an opening serving as the radiation-transmissive means at the sample supporting means.

7. The accessory of claim 1, wherein the enclosure outside wall is a top horizontally oriented wall and the ellipsoidal segments are vertically oriented.

8. The accessory of claim 7, wherein the first and second plane reflectors are mounted generally at the enclosure center inside of the ellipsoidal segments.

9. A variable angle reflection accessory for use in reflection spectrometry, comprising:

an accessory housing having walls including an outside wall having radiation-transmissive means and a sample support surface on its outside for receiving a sample having a surface to reflect a radiation beam, first and second ellipsoidal segment reflectors fixedly mounted inside the housing adjacent the sample supporting surface and in positions at the left and right sides of the sample supporting surface such that each ellipsoidal segment defines a first focus substantially at a sample on said surface and a second focus at, respectively, the left and right sides of a sample on said surface, first and second plane reflectors rotatably mounted inside the housing and positioned, respectively, at the left and right sides each with its reflecting surface at the location, respectively, of the second focus of the first and second ellipsoidal segments, optical means for directing a converging beam of radiation from a spectrometer to a focus at the first plane reflector and for directing a diverging radiation beam from the second plane reflector back to the spectrometer, means for rotating the first and second plane reflectors in unison but in opposite directions so as to cause the radiation beam incident on the first plane reflector to scan across the surface of the first ellipsoidal segment whereby the beam reflected from the latter is incident on a sample on the sample supporting surface at an angle of incidence that varies with the degree of rotation of the first plane reflector.

10. A variable angle reflection accessory as claimed in claim 9, wherein the optical means for directing the radiation beam to the first plane reflector comprises at least one plane mirror for intersecting the radiation beam from the spectrometer.

11. A variable angle reflection accessory as claimed in claim 10, wherein the optical means for returning the beam to the spectrometer comprises at least one plane mirror.

12. A variable angle reflection accessory as claimed in claim 11, wherein the ellipsoidal segment reflector, plane reflector, and optical means mounted to the left of the sample supporting surface are the same as those mounted to the right but in mirror image positions.

13. A variable angle reflection accessory as claimed in claim 9, further comprising a rotary scale for indicating the angle of incidence, and means connecting said scale to said means for rotating said first and second plane reflectors.

14. A variable angle reflection accessory as claimed in claim 13, wherein the scale is linear, and said means for rotating comprises a knob connected to the scale and operable by the user.

15. A variable angle reflection accessory as claimed in claim 14, wherein said knob has an arcuate slot, first and second shafts supporting said first and second plane reflectors for rotation, each of said first and second shafts comprising, respectively, first and second pins engaging the arcuate slot and moveable when said knob is rotated.

16. A variable angle reflection accessory as claimed in claim 15, further comprising a third pin interconnecting the ends of the first and second pins and engaging the slot and operable to rotate the shafts when the knob is rotated.

17. A variable angle reflection accessory as claimed in claim 16, wherein the pins and slot are configured such that a linear relationship is established between angular rotation of the knob and angular rotation of the first and second plane reflectors.

* * * * *